(12) United States Patent
Thurk

(10) Patent No.: US 7,081,447 B2
(45) Date of Patent: Jul. 25, 2006

(54) ORGANIC COMPOUNDS WITH BIOLOGICAL ACTIVITY AS THROMBIN INHIBITORS AND USE THEREOF

(75) Inventor: Marcel Thurk, Bovenden (DE)

(73) Assignee: Novel Science International GmbH, Gottingen (DE)

( * ) Notice: Subject to any disclaimer, the term of this patent is extended or adjusted under 35 U.S.C. 154(b) by 0 days.

(21) Appl. No.: 10/798,218

(22) Filed: Mar. 10, 2004

(65) Prior Publication Data

US 2005/0026843 A1    Feb. 3, 2005

Related U.S. Application Data

(63) Continuation of application No. PCT/EP02/10137, filed on Sep. 10, 2002.

(30) Foreign Application Priority Data

| Sep. 10, 2001 | (DE) | ................................ | 101 44 340 |
| Sep. 21, 2001 | (DE) | ................................ | 101 46 632 |
| Oct. 9, 2001 | (DE) | ................................ | 101 49 678 |
| Nov. 21, 2001 | (DE) | ................................ | 101 56 995 |
| Jan. 10, 2002 | (DE) | ................................ | 102 00 666 |

(51) Int. Cl.
| A61K 38/08 | (2006.01) |
| A61K 38/07 | (2006.01) |
| C07K 7/04 | (2006.01) |
| C07K 5/10 | (2006.01) |
| C07K 1/00 | (2006.01) |

(52) U.S. Cl. .............................. 514/17; 514/2; 514/18; 530/300; 530/329; 530/330; 530/333

(58) Field of Classification Search ................ 530/300
See application file for complete search history.

(56) References Cited

U.S. PATENT DOCUMENTS 4,440,678 A  *  4/1984  Svendsen .................... 530/331

6,197,541 B1  *  3/2001  Coughlin .................... 435/69.1

FOREIGN PATENT DOCUMENTS

| EP | 0 456 152 A2 | 11/1991 |
| EP | 0 498 508 A1 | 8/1992 |
| EP | 0 531 537 A1 | 3/1993 |
| WO | WO-92/13879 A1 | 8/1992 |

OTHER PUBLICATIONS

J. Rudinger. In: Peptide Hormones, JA Parsons, Ed. (1976) 1-7.*
D. Voet and J.G. Voet. Biochemistry, 2nd Edition.(1995), pp. 235-241.*
D.E. Smilek, et al. Proc. Natl. Acad. Sci. USA (1991) 88. pp. 9633-9637.*
W.S. Messer, "Vasopressin and Oxytocin", web document updated Apr. 3, 2000; http://www.neurosci.pharm.utoledo.edu/MBC3320/vasopressin.htm; 5 pages.*
R.J. Bastin, et al. Org. Proc. Res. Dev. (2000) 4, 427-435.*
Goran Glaeson, "Synthetic peptides and peptidomimetics as substrates and inhibitors of thrombin and other proteases in the blood coagulation system", Blood Coagulation & Fubrunolysis, Rapid Communications, Oxford GB, 5, (1994) pp. 411-436.

* cited by examiner

*Primary Examiner*—Bruce R. Campbell
*Assistant Examiner*—Andrew D. Kosar

(74) *Attorney, Agent, or Firm*—Darby & Darby

(57) ABSTRACT

The invention relates to biologically active molecules, interacting with thrombin and inhibiting the same. The invention particularly relates to molecules of general formula: $Y^1$—(NH—$X^1$—C=O)—(NH—$X^2$—C=C)—(NH—$X^3$—C=O)NH—$X^4$—C=O)—(NH—$X^5$—C=O)—(NH—$X^6$—C=O)—$Y^2$, in which $Y^1$, $Y^2$, and $X^{1-6}$ have the meanings given in the description, N or C-terminal shortened variants of said compounds and the use thereof for the production of medicaments.

4 Claims, No Drawings

SEQUENCE LISTING

<160> NUMBER OF SEQ ID NOS: 1

<210> SEQ ID NO 1
<211> LENGTH: 12
<212> TYPE: PRT
<213> ORGANISM: artificial
<220> FEATURE:
<223> OTHER INFORMATION: synthetic protein

<400> SEQUENCE: 1

Asn Gly Asp Phe Glu Glu Ile Pro Gln Gln Tyr Leu
1               5                   10

ORGANIC COMPOUNDS WITH BIOLOGICAL ACTIVITY AS THROMBIN INHIBITORS AND USE THEREOF

This invention relates to active biological substances that interact with thrombin and inhibit it. The substances are useful as anticoagulants for humans and animals. The invention also relates to compositions and combinations with these substances for therapeutic, prophylactic, and diagnostic purposes.

Acute vascular diseases such as myocardial infarction, stroke, pulmonary embolism, deep vein thrombosis, or peripheral vascular occlusion and other thromboses of the circulatory system, constitute an important source of health risks. Such diseases are brought about by complete or partial occlusion of the blood vessel by a thrombus that contains fibrin and blood platelets.

Present methods for the treatment and prophylaxis of such thrombotic diseases include therapeutics that act in two different ways. The first type of therapeutic prevents thrombin activity or thrombogenesis and thus the formation of the thrombus. These drugs also prevent the development of platelets and their aggregation. The second category of drugs accelerates thrombolysis and breaks up the thrombus, thus removing it from the blood vessel, and eliminates the blockage of blood flow.

Heparin and coumarin, preparations of the first type, are used widely to treat venous thrombotic embolisms in which thrombotic activity is responsible for the development and expansion of the thrombus. Although effective, heparin nevertheless brings about many adverse side effects such as hemorrhaging or thrombocytopenia. The same is true of coumarin, which acts by blocking or preventing the formation of prothrombin and needs some time for its full action to be deployed. Taken together, this has led to a search for anticoagulants that have more specific activity and are less toxic, for example peptidic inhibitors.

Hirudin is a naturally occurring polypeptide that is produced by the leech Hirudo medicinalis. This active substance, which is synthesized in the salivary glands of the leech, is the most fully effective known natural anticoagulant. Hirudin is a direct thrombin inhibitor and prevents the coagulation of blood by binding strongly to thrombin ($Kd=2\times10^{-14}$ M) in a stoichiometric 1:1 complex [Stone & Hofstenge, Kinetics of the inhibition of thrombin by hirudin, Biochemistry 25, pp. 4622–4628 (1986)]. This in turn prevents thrombin from catalyzing the conversion of fibrinogen to fibrin (the thrombus), in the same way as it also prevents all other thrombin-mediated cleavage processes.

The efficiency of hirudin obtained in purified form from leeches in the prevention of venous thromboses, vascular occlusion, and thrombin-induced disseminated intravascular coagulation, has been demonstrated in animal studies. Furthermore, hirudin shows low toxicity, little antibody formation, and rapid degradability from the circulatory system [F. Markwardt et al., Pharmacological studies on the antithrombic action of hirudin in experimental animals, Thromb. Haemost. 47, pp. 226–229 (1982)]. In projects with the intention of producing larger amounts of hirudin, attempts have been made to prepare the polypeptide by recombinant DNA technology. The presence of an O-sulfated tyrosine residue in natural hirudin and the inability of microorganisms to carry out a modification of the same type, made the prospects of recombinant production of biologically active hirudin highly speculative. The observation that desulfated hirudin is almost as effective as the sulfated counterpart [U.S. Pat. No. 4,654,302] showed the path toward cloning and preparation in various expression systems, including S. cerevisiae [Harvey et al., Cloning and expression of cDNA coding for the anticoagulant hirudin from the bloodsucking leech, Hirudo medicinalis, PNAS 83, pp. 1084–1088; Europ. Pat. Appl. 158 654, 168 342, and 171 024], E. coli [Bergmann et al., Chemical synthesis and expression of a gene coding for hirudin, the thrombin-specific inhibitor from the leech Hirudo medicinalis, Biol. Chem. Hoppe-Seyler 367, pp. 731–740; Europ. Pat. Appl. 200 655], and on the tips of a filamentous phage as a fusion protein with Protein III (pIII) [Wirsching et al., Display of functional thrombin inhibitor hirudin on the surface of phage M13, Gene 204, pp. 177–184]. Despite these advances, hirudin in production is truly expensive, now as ever. Nevertheless, it has passed through the third clinical phase and was recently permitted for the treatment of heparin-induced thrombocytopenia (HMR).

Only recently was there success in identifying peptide fragments of natural hirudin that prolong coagulation time in the same way. However, such peptide fragments cannot be fully satisfactory because of their low efficacy with regard to preventing thrombogenesis. Thus, N-acetylhirudin$_{45-65}$ has an efficacy lower by four orders of magnitude than natural hirudin, although now as before it is still a relatively large molecule. The problem of less affinity for thrombin has been solved by the development of hirulogs [U.S. Pat. No. 5,433,940]. These molecules can imitate the action of hirudin by binding both to the lower-affinity outward-facing anion-binding side and to the catalytic side of α-thrombin. From there, hirulogs are characterized by a half associated with the anion-binding outside of thrombin, a connecting group, and a portion oriented toward the catalytic center of thrombin. The most preferred hirulog is hirulog-8, a peptide consisting of 20 amino acids that is made up of the peptide D-Phe-Pro-Arg-Pro- inhibiting the catalytic center, a Gly$_4$ connecting sequence, and the sequence -Asn-Gly-Asp-Phe-Glu-Glu-Ile-Pro-Glu-Glu-Tyr-Leu-OH of hirudin. Hirulog-8 has recently arrived on the market in the USA.

Despite the advances of relatively high efficacy for thrombin ($K_i=2.3$ nM), hirulogs are still relatively large molecules that have to be synthesized in relatively cumbersome schemes such as mixed heterologous/solid phases. Like hirudin, hirulogs are useful only parenterally and have to be carefully monitored. For this reason hirulogs are not suitable as lead structures for small molecules that ultimately could also be administered orally.

Therefore, there have been some efforts to identify smaller peptides as potent thrombin inhibitors. Bettelheim, as early as 1956, showed that fibrinopeptide A comparably inhibits the reaction between thrombin and fibrinogen. Joint research by Blombäck and Nobel Pharma/Kabi in Stockholm found peptide sequences derived from fibrinopeptide A with no more than nine amino acids with good efficacy on thrombin. Essential components for efficacy were an N-terminal Phe and a C-terminal Arg, separated by seven amino acids. Fewer amino acids reduced efficacy, but astonishingly a tripeptide with N- and C-terminal Phe and Arg, respectively, showed excellent efficacy. The best tripeptide with inhibiting action on the thrombin-fibrinogen reaction was Bz-Phe-Val-Arg-OMe, wherein Val precedes Arg as in the full-length fibrinopeptide [Blombäck et al., Synthetic peptides with anticoagulant and vasodilating activity, Scand. J. Clin. Lab. Invest. 24, pp. 59–66 (1969), U.S. Pat. No. 3,826,794 (1974)]. In contrast to fibrinopeptide A, Pro precedes Arg in a number of other thrombin fragment regions, like that of prothrombin, of Factor XIII, and of human growth hormone. Most of today's most effective thrombin-inhibiting peptides and peptidomimetics were developed on the basis of the Pro-Arg sequence. Among these most effective inhibitors is H-D-Phe-Pro-Arg-H ($K_i$=70 nM) [Bajuz et al., Inhibition of thrombin and trypsin by tripeptide aldehydes, Int. J. Peptide Protein Res. 12, pp. 217–221 (1978); Hung. Pat. 169 870 (1974)]. The conception of this protein grew from the discovery of peptide aldehydes of bacterial origin by H. Umezawa. These so-called leupeptides (e.g. Ac-Leu-Leu-Arg-H) are inhibitors of plasmin and of other trypsin-like proteases, but not of thrombin. The aldehyde carbon in its acetal form has a tetrahedral structure like the carbonyl carbon of substrates in the transition phase.

From these aldehydes just mentioned, Shaw et al. synthesized the irreversible chloromethyl ketone inhibitor H-D-Phe-Pro-Arg-CH$_2$—Cl with a $K_i$ of 25 nM [Kettner et al., H-D-Phe-Pro-Arg-CH$_2$—Cl— a selective activity label for thrombin, Thromb. Res. 14, pp. 969–973 (1979)]. Development work at Eli Lilly led to N-D-Methyl-Phe-Pro-Arg-H, also known as Efegatran [tm]. The D-Phe-Pro-Arg sequence has recently been again developed further. Speculations that an N-terminal amino acid with aromatic/lipophilic groups might produce greater efficacy against thrombin led to the discovery of some inhibitors with new amino acids at this position, including β,β-diphenylalanine (Dpa), phenylglycine, cyclohexylglycine, carboxy-1,2,3,4-tetrahydroisoquinoline (Tiq) [Schuman et al., Highly selective thrombin inhibitors, J. Med. Chem. 36, pp. 314–319 (1993)]. The most interesting compound was D-1-Tiq-Pro-Arg-H, which produced twice the gain in efficacy compared with Boc-D-Phe-Pro-Arg-H. However, trypsin is inhibited to the same degree as thrombin.

From the data available today, it is clear that although there are some effective anticoagulant compounds, a need exists for powerful antithrombins that act quickly to prevent thrombogenesis and that do not interfere with other protease activities, for example the action of plasmin in breaking up the thrombus.

Considering this state of the art, the task underlying this invention was to make available compounds that are biologically active in the sense of thrombin inhibition, and that avoid the drawbacks of the prior art described above. The problem underlying the invention also consisted of inhibiting thrombin specifically at low drug concentrations and with low cell toxicity.

This task is accomplished with the compounds (I), (II), (III), (IV), and (V) defined below.

In a first version, the above task is accomplished by the compound with the formula

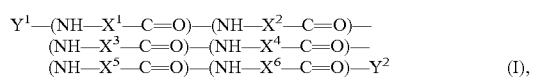

(I), wherein $Y^1$ is either
1. a hydrogen or
2. a methyl group or
3. an acetyl group or
4. is characterized by a backbone consisting of a chain of 1 to 32 carbon atoms, wherein (NH—X$_1$—C=O) is a basic amino acid residue, preferably
1. L-arginine or
2. D-arginine or
3. L-lysine or
4. D-lysine or
5. L-ornithine or
6. D-ornithine, wherein (NH—X$^2$—C=O) is a cyclic, nonpolar amino acid, preferably
1. L-cyclohexylalanine or
2. D-cyclohexylalanine or
3. L-cyclohexylglycine or
4. D-cyclohexylglycine, wherein (NH—X$^3$—C=O) is any arbitrary D- or L-amino acid, preferably
1. L-norleucine or
2. D-norleucine or
3. L-leucine or
4. D-leucine or
5. L-isoleucine or
6. D-isoleucine or
7. L-cyclohexylalanine or
8. D-cyclohexylalanine or
9. L-cyclohexylglycine or
10. D-cyclohexylglycine or
11. L-proline or
12. D-proline or
13. L-aspartic acid or
14. D-aspartic acid or
15. L-glutamic acid or
16. D-glutamic acid, wherein (NH—X$^4$—C=O) is a cyclic D- or L-amino acid, preferably
1. L-cyclohexylalanine or
2. D-cyclohexylalanine or
3. L-cyclohexylglycine or
4. D-cyclohexylglycine or
5. L-tyrosine or
6. D-tyrosine or
7. L-phenylalanine or
8. D-phenylalanine, wherein (NH—X$^5$—C=O) is an amino acid with a polar side chain, preferably
1. L-glutamine or
2. D-glutamine or
3. L-ornithine or
4. D-ornithine or
5. L-glutamic acid or
6. D-glutamic acid or
7. L-arginine or
8. D-arginine or
9. L-lysine or
10. D-lysine or
11. L-asparagine or
12. D-asparagine or
13. L-aspartic acid or
14. D-aspartic acid or
15. is replaced by a chemical bond, wherein (NH—X$^6$—C=O) is any arbitrary D- or L-amino acid, preferably
1. L-arginine or
2. D-arginine or
3. is replaced by a chemical bond, wherein $Y^2$ is either
1. an OH group (the C-terminal amino acid has a terminal carboxylic acid group) or
2. an amino group (the carboxylic acid group in the C-terminal amino acid is replaced by an amide group) or
3. a hydrogen (the carboxylic acid group in the C-terminal amino acid is replaced by an aldehyde group) or 4. 7-amido-4-methylcoumarin (combined through the carboxylic acid group) or
5. para-nitroanilide (combined through the carboxylic acid group) or
6. is replaced by a connecting chain containing 1 to 35 atoms, or is a molecule shortened at the C-terminus and/or at the N-terminus by not less than one amino acid, and pharmaceutically acceptable salts thereof.

The invention also relates to derivatives of the aforementioned compounds of Formula (I).

Especially beneficial results are produced when the peptide of Formula (I) pursuant to the invention is N-acetyl-L-Arg-L-Cha-(NH—X$^3$—C=O)-L-Cha-(NH—X$^5$—C=O) amide or N-acetyl-L-Arg-L-Cha-(NH—X$^3$—C=O)-L-Cha amide or N-acetyl-L-Arg-L-Cha-(NH—X$^3$—C=O)-D-Tyr-(NH—X$^5$—C=O) amide.

In a second version, the above task is accomplished by the compound with the formula

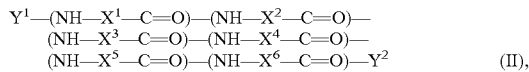

$$Y^1—(NH—X^1—C=O)—(NH—X^2—C=O)—\\(NH—X^3—C=O)—(NH—X^4—C=O)—\\(NH—X^5—C=O)—(NH—X^6—C=O)—Y^2 \quad (II),$$

wherein $Y^1$ is either
1. a hydrogen or
2. a methyl group or
3. an acetyl group or
4. is characterized by a backbone consisting of a chain of 1 to 32 carbon atoms, wherein (NH—$X_1$—C=O) is a D- or L-amino acid, preferably
1. valine or
2. alanine or
3. leucine or
4. isoleucine or
5. norleucine or
6. aspartic acid or
7. glutamic acid or
8. serine or
9. threonine or
10. tyrosine or
11. arginine or
12. lysine or
13. ornithine or
14. is replaced by a chemical bond, wherein (NH—X$^2$—C=O) is a D- or L-amino acid, preferably
1. alanine or
2. valine or
3. leucine or
4. isoleucine or
5. norleucine or
6. serine or
7. threonine or
8. tyrosine or
9. proline or
10. citrulline or
11. arginine or
12. lysine or
13. ornithine or
14. cyclohexylalanine or
15. cyclohexylglycine or
16. is replaced by a chemical bond, wherein (NH—X$^3$—C=O) is any arbitrary amino acid, for example
1. L-cyclohexylalanine or
2. D-cyclohexylalanine or
3. L-cyclohexylglycine or
4. D-cyclohexylglycine, wherein (NH—X$^4$—C=O) is a small amino acid, preferably
1. L-proline or
2. D-proline or
3. is replaced by a chemical bond, wherein (NH—X$^5$—C=O) is a preferably aromatic amino acid such as
1. L-tyrosine or
2. D-tyrosine or
3. L-phenylalanine or
4. D-phenylalanine or
5. is replaced by a chemical bond, wherein (NH—X$^6$—C=O) is an amino acid with a basic side chain, preferably
1. L-arginine or
2. D-arginine or
3. L-lysine or
4. D-lysine or
5. L-ornithine or
6. D-ornithine, wherein $Y^2$ is either
1. an OH group (the C-terminal amino acid has a terminal carboxylic acid group) or
2. an amino group (the carboxylic acid group in the C-terminal amino acid is replaced by an amide group) or
3. a hydrogen (the carboxylic acid group in the C-terminal amino acid is replaced by an aldehyde group) or
4. 7-amido-4-methylcoumarin (combined through the carboxylic acid group) or
5. para-nitroanilide (combined through the carboxylic acid group) or
6. is replaced by a connecting chain containing 1 to 35 atoms, or is a molecule shortened at the C-terminus and/or at the N-terminus by not less than one amino acid, and pharmaceutically acceptable salts thereof.

The invention also relates to derivatives of the aforementioned compounds of Formula (II).

Especially beneficial results are produced when the peptide of Formula (II) pursuant to the invention is N-acetyl-D-Val-L-Ala-L-Cha-D-Pro-D-Tyr-L-Arg amide, N-acetyl-L-Asp-L-Ser-L-Cha-D-Pro-D-Tyr-L-Arg amide, N-acetyl-L-Ile-L-Cha-D-Pro-D-Tyr-L-Arg amide, N-acetyl-D-Val-L-Cha-D-Pro-D-Tyr-L-Arg amide, N-acetyl-L-Ser-L-Ser-L-Cha-D-Pro-D-Tyr-L-Arg amide, N-acetyl-D-Lys-D-Pro-L-Cha-D-Pro-D-Tyr-L-Arg amide, N-acetyl-L-Tyr-L-Cit-L-Cha-D-Pro-D-Tyr-L-Arg amide, N-acetyl-L-Ser-D-Val-L-Cha-D-Pro-D-Tyr-L-Arg amide, N-acetyl-L-Ser-L-Ala-L-Cha-D-Pro-D-Tyr-L-Arg amide, N-acetyl-L-Ser-L-Arg-L-Cha-D-Pro-D-Tyr-L-Arg amide, N-acetyl-L-Ser-L-Cha-L-Cha-D-Pro-D-Tyr-L-Arg amide, N-acetyl-D-Lys-L-Nle-L-Cha-D-Pro-D-Tyr-L-Arg amide, N-acetyl-L-Arg-L-Cha-D-Pro-D-Tyr-L-Arg amide, N-acetyl-L-Ser-L-Cha-D-Pro-D-Tyr-L-Arg amide, N-acetyl-L-Ser-D-Glu-L-Cha-D-Pro-D-Tyr-L-Arg amide, or N-acetyl-D-Tyr-L-Cha-D-Pro-D-Tyr-L-Arg amide.

In a third version, the above task is accomplished by the compound with the formula

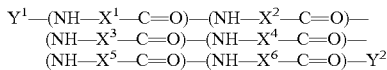
(III), wherein $Y^1$ is either
1. a hydrogen or
2. a methyl group or
3. an acetyl group or
4. is characterized by a backbone consisting of a chain of 1 to 32 carbon atoms, wherein $(NH-X_1-C=O)$ is a D- or L-amino acid, preferably
1. valine or
2. alanine or
3. leucine or
4. isoleucine or
5. norleucine or
6. asparagine or
7. glutamine or
8. serine or
9. threonine or
10. tyrosine or
11. arginine or
12. lysine or
13. ornithine or
14. is replaced by a chemical bond, wherein $(NH-X^2-C=O)$ is a D- or L-amino acid, preferably
1. alanine or
2. valine or
3. leucine or
4. isoleucine or
5. norleucine or
6. serine or
7. threonine or
8. tyrosine or
9. proline or
10. citrulline or
11. arginine or
12. lysine or
13. ornithine or
14. histidine or
15. glutamic acid or
16. aspartic acid or
17. tryptophan or
18. cyclohexylalanine or
19. cyclohexylglycine or
20. is replaced by a chemical bond, wherein $(NH-X^3-C=O)$ is any arbitrary amino acid, for example
1. L-cyclohexylalanine or
2. D-cyclohexylalanine or
3. L-cyclohexylglycine or
4. D-cyclohexylglycine, wherein $(NH-X^4-C=O)$ is a small amino acid, preferably
1. L-proline or
2. D-proline or
3. is replaced by a chemical bond, wherein $(NH-X^5-C=O)$ is a preferably aromatic amino acid such as
1. L-tyrosine or
2. D-tyrosine or
3. L-phenylalanine or
4. D-phenylalanine or
5. is replaced by a chemical bond, wherein $(NH-X^6-C=O)$ is an amino acid with a basic side chain, preferably
1. L-arginine or
2. D-arginine or
3. L-lysine or
4. D-lysine or
5. L-ornithine or
6. D-ornithine, wherein $Y^2$ is either
1. an OH group (the C-terminal amino acid has a terminal carboxylic acid group) or
2. an amino group (the carboxylic acid group in the C-terminal amino acid is replaced by an amide group) or
3. a hydrogen (the carboxylic acid group in the C-terminal amino acid is replaced by an aldehyde group) or
4. 7-amido-4-methylcoumarin (combined through the carboxylic acid group) or
5. para-nitroanilide (combined through the carboxylic acid group) or
6. is replaced by a connecting chain containing 1 to 35 atoms, or is a molecule shortened at the C-terminus and/or at the N-terminus by not less than one amino acid, and pharmaceutically acceptable salts thereof.

The invention also relates to derivatives of the aforementioned compounds of Formula (III).

Especially beneficial results are produced when the peptide of Formula (III) pursuant to the invention is N-acetyl-D-Gln-D-His-L-Cha-D-Pro-D-Tyr-L-Arg amide, N-acetyl-D-Glu-L-Cha-D-Pro-D-Tyr-L-Arg amide, N-acetyl-D-Val-D-His-L-Cha-D-Pro-D-Tyr-L-Arg amide, N-acetyl-L-Ala-L-Cha-D-Pro-D-Tyr-L-Arg amide, N-acetyl-L-Ile-L-Arg-L-Cha-D-Pro-D-Tyr-L-Arg amide, N-acetyl-L-Tyr-L-Cit-L-Cha-D-Pro-D-Tyr-L-Arg amide, N-acetyl-L-Ser-L-Ser-L-Cha-D-Pro-D-Tyr-L-Arg amide, N-acetyl-D-Val-L-Cha-D-Pro-D-Tyr-L-Arg amide, N-acetyl-L-Trp-L-Cha-D-Pro-D-Tyr-L-Arg amide, N-acetyl-L-Ser-L-Ala-L-Cha-D-Pro-D-Tyr-L-Arg amide, N-acetyl-L-Ser-L-Arg-L-Cha-D-Pro-D-Tyr-L-Arg amide, N-acetyl-D-Lys-L-Nle-L-Cha-D-Pro-D-Tyr-L-Arg amide, N-acetyl-D-Tyr-L-Cha-D-Pro-D-Tyr-L-Arg amide, N-acetyl-L-Arg-L-Cha-D-Pro-D-Tyr-L-Arg amide, or N-acetyl-L-Tyr-D-Pro-L-Cha-D-Pro-D-Tyr-L-Arg amide.

In a fourth version, the above task is accomplished by the compound with the formula

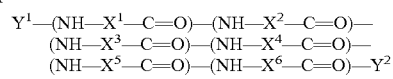
(IV), wherein $Y^1$ is either
1. a hydrogen or
2. a methyl group or
3. an acetyl group or
4. is characterized by a backbone consisting of a chain of 1 to 32 carbon atoms, wherein $(NH-X_1-C=O)$ is a D- or L-amino acid, preferably
1. valine or
2. alanine or
3. leucine or
4. isoleucine or
5. norleucine or
6. asparagine or
7. glutamine or 8. serine or
9. threonine or
10. tyrosine or
11. arginine or
12. lysine or
13. ornithine or
14. is replaced by a chemical bond, wherein (NH—$X^2$—C=O) is a D- or L-amino acid, preferably
1. alanine or
2. valine or
3. leucine or
4. isoleucine or
5. norleucine or
6. serine or
7. threonine or
8. tyrosine or
9. proline or
10. citrulline or
11. arginine or
12. lysine or
13. ornithine or
14. histidine or
15. glutamic acid or
16. aspartic acid or
17. tryptophan or
18. cyclohexylalanine or
19. cyclohexylglycine or
20. is replaced by a chemical bond, wherein (NH—$X^3$—C=O) is any arbitrary amino acid, for example
1. L-cyclohexylalanine or
2. D-cyclohexylalanine or
3. L-cyclohexylglycine or
4. D-cyclohexylglycine, wherein (NH—$X^4$—C=O) is a small amino acid, preferably
1. L-proline or
2. D-proline or
3. L-azetidine-2-carboxylic acid or
4. D-azetidine-2-carboxylic acid, wherein (NH—$X^5$—C=O) is a preferably aromatic amino acid such as
1. L-tyrosine or
2. D-tyrosine or
3. L-phenylalanine or
4. D-phenylalanine, wherein (NH—$X^6$—C=O) is an amino acid with a basic side chain, preferably
1. L-arginine or
2. D-arginine or
3. L-lysine or
4. D-lysine or
5. L-ornithine or
6. D-ornithine or
7. L-homoarginine or
8. D-homoarginine, wherein $Y^2$ is either
1. an OH group (the C-terminal amino acid has a terminal carboxylic acid group) or
2. an amino group (the carboxylic acid group in the C-terminal amino acid is replaced by an amide group) or
3. a hydrogen (the carboxylic acid group in the C-terminal amino acid is replaced by an aldehyde group) or
4. 7-amido-4-methylcoumarin (combined through the carboxylic acid group) or
5. para-nitroanilide (combined through the carboxylic acid group) or
6. is replaced by a connecting chain containing 1 to 35 atoms,
or is a molecule shortened at the C-terminus and/or at the N-terminus by not less than one amino acid, and pharmaceutically acceptable salts thereof.

The invention also relates to derivatives of the aforementioned compounds of Formula (IV).

Especially beneficial results are produced when the peptide of Formula (IV) pursuant to the invention is N-acetyl-D-Gln-D-His-L-Cha-D-Pro-D-Tyr-L-Arg amide, N-acetyl-D-Glu-L-Cha-D-Pro-D-Tyr-L-Arg amide, N-acetyl-D-Val-D-His-L-Cha-D-Pro-D-Tyr-L-Arg amide, N-acetyl-L-Ala-L-Cha-D-Pro-D-Tyr-L-Arg-amide, N-acetyl-L-Ile-L-Arg-L-Cha-D-Pro-D-Tyr-L-Arg amide, N-acetyl-L-Tyr-L-Cit-L-Cha-D-Pro-D-Tyr-L-Arg amide, N-acetyl-L-Ser-L-Ser-L-Cha-D-Pro-D-Tyr-L-Arg amide, N-acetyl-D-Val-L-Cha-D-Pro-D-Tyr-L-Arg amide, N-acetyl-L-Trp-L-Cha-D-Pro-D-Tyr-L-Arg amide, N-acetyl-L-Ser-L-Ala-L-Cha-D-Pro-D-Tyr-L-Arg amide, N-acetyl-L-Ser-L-Arg-L-Cha-D-Pro-D-Tyr-L-Arg amide, N-acetyl-D-Lys-L-Nle-L-Cha-D-Pro-D-Tyr-L-Arg amide, N-acetyl-D-Tyr-L-Cha-D-Pro-D-Tyr-L-Arg amide, N-acetyl-L-Arg-L-Cha-D-Pro-D-Tyr-L-Arg amide, N-acetyl-L-Tyr-D-Pro-L-Cha-D-Pro-D-Tyr-L-Arg amide, N-acetyl-L-Ala-D-Cha-L-Aze-D-Tyr-L-Arg amide, N-acetyl-L-Ala-D-Cha-L-Pro-D-Tyr-L-Har amide, or N-acetyl-L-Ala-D-Cha-L-Aze-D-Tyr-L-Har amide.

In a fifth version, the above task is accomplished by the compound with the formula $$Y^1\text{—(NH—}X^1\text{—C=O)—(NH—}X^2\text{—C=O)—}$$
$$\text{(NH—}X^3\text{—C=O)—(NH—}X^4\text{—C=O)—}$$
$$\text{(NH—}X^5\text{—C=O)—(NH}X^6\text{—C=O)—}Y^2 \quad (V),$$

wherein $Y^1$ is either
1. a hydrogen or
2. a methyl group or
3. an acetyl group or
4. is characterized by a backbone consisting of a chain of 1 to 32 carbon atoms, wherein (NH—$X_1$—C=O) is a D- or L-amino acid, preferably
1. valine or
2. alanine or
3. leucine or
4. isoleucine or
5. norleucine or
6. asparagine or
7. glutamine or
8. serine or
9. threonine or
10. tyrosine or
11. arginine or
12. lysine or
13. ornithine or
14. phenylalanine or
15. dichlorophenylalanine or
16. tetrahydronorharman-3-carboxylic acid or
17. 1,2,3,4-tetrahydroisoquinoline-3-carboxylic acid or
18. 4-phenylpiperidine-4-carboxylic acid or
19. thienylalanine or
20. phenylglycine or
21. p-nitrophenylalanine or
22. is replaced by a chemical bond, wherein (NH—X²—C═O) is a D- or L-amino acid, preferably
1. alanine or
2. valine or
3. leucine or
4. isoleucine or
5. norleucine or
6. serine or
7. threonine or
8. tyrosine or
9. proline or
10. citrulline or
11. arginine or
12. lysine or
13. ornithine or
14. histidine or
15. glutamic acid or
16. aspartic acid or
17. tryptophan or
18. cyclohexylalanine or
19. cyclohexylglycine or
20. is replaced by a chemical bond, wherein (NH—X³—C═O) is any arbitrary amino acid, for example
1. L-cyclohexylalanine or
2. D-cyclohexylalanine or
3. L-cyclohexylglycine or
4. D-cyclohexylglycine, wherein (NH—X⁴—C═O) is a small amino acid, preferably
1. L-proline or
2. D-proline or
3. L-azetidine-2-carboxylic acid or
4. D-azetidine-2-carboxylic acid, wherein (NH—X⁵—C═O) is a preferably aromatic amino acid such as
1. L-tyrosine or
2. D-tyrosine or
3. L-phenylalanine or
4. D-phenylalanine, wherein (NH—X⁶—C═O) is an amino acid with a basic side chain, preferably
1. L-arginine or
2. D-arginine or
3. L-lysine or
4. D-lysine or
5. L-ornithine or
6. D-ornithine or
7. L-homoarginine or
8. D-homoarginine, wherein Y² is either
1. an OH group (the C-terminal amino acid has a terminal carboxylic acid group) or
2. an amino group (the carboxylic acid group in the C-terminal amino acid is replaced by an amide group) or
3. a hydrogen (the carboxylic acid group in the C-terminal amino acid is replaced by an aldehyde group) or
4. 7-amido-4-methylcoumarin (combined through the carboxylic acid group) or
5. para-nitroanilide (combined through the carboxylic acid group) or
6. is replaced by a connecting chain containing 1 to 35 atoms, or is a molecule shortened at the C-terminus and/or at the N-terminus by not less than one amino acid, and pharmaceutically acceptable salts thereof.

The invention also relates to derivatives of the aforementioned compounds of Formula (V).

Especially beneficial results are produced when the peptide of Formula (V) pursuant to the invention is N-acetyl-R₁-L-Cha-D-Pro-D-Tyr-L-Arg amide, wherein R₁ stands for D-Gln-D-His, D-Glu, D-Val-D-His, L-Ala, L-Ile-L-Arg, L-Tyr-L-Cit, L-Ser-L-Ser, D-Val, L-Trp, L-Ser-L-Ala, L-Ser-L-Arg, D-Lys-L-Nle, D-Tyr, L-Arg, or L-Tyr-D-Pro, [and] when the peptide pursuant to the invention is N-acetyl-L-Ala-D-Cha-L-Aze-D-Tyr-L-Arg amide, N-acetyl-L-Ala-D-Cha-L-Pro-D-Tyr-L-Har amide, or N-acetyl-R₂-D-Cha-L-Aze-D-Tyr-Har amide, wherein R₂ stands for L-Trp, L-Ala, D-Phe, L-Dcp, L-Nhm, L-Iq3, L-Ppd, L-Tea, L-Phg, L-Nle, L-Cha, or L-Pnp.

The compounds pursuant to the invention can be used to inhibit all thrombin-mediated or thrombin-associated functions and processes. Pharmaceutical compositions that contain these compounds as well as methods for the treatment and prophylaxis of vascular diseases, inflammatory reactions, carcinomas, and neurodegenerative diseases that use these compounds are also objects of this invention. The compounds can also be used for ex vivo preparation, for the storage and treatment of blood outside the body, and for coating invasive equipment. The compounds can also be administered to a patient (patient in this context means a human or an animal) in combination with a fibrinolytic agent to increase the efficacy of a given dose or to reduce the dose necessary to produce a desired effect, such as disintegrating blood clots or preventing the re-occlusion of the previously blocked blood vessel.

Because of its high potential and the fact that it can be prepared by chemical synthesis techniques, the compounds can be produced economically in commercially practical amounts. The peptides are converted into suitable salt forms such as acetates and sulfates.

Furthermore, the molecules pursuant to the invention are substantially smaller than hirudin and the other peptidic thrombin inhibitors described up to now. For this reason they are more unlikely to cause an adverse reaction of the immune system of patients treated with these substances. Accordingly, the use of these thrombin inhibitors is not limited to the treatment of acute disorders. These compounds can also be used in the therapy of chronic thromboembolic diseases such as arteriosclerosis or re-stenosis consequent to angioplasty. The compounds pursuant to the invention can also be used in a number of other applications instead of natural and recombinant thrombin.

It can be concluded from the disclosure that the compounds, compositions, and methods pursuant to the invention are useful for the treatment and care of various diseases in connection with adverse effects of thrombin, and also for diagnostic purposes.

Finally, it should be mentioned that the molecules of this invention can serve as lead structures for the development of molecules with even more beneficial properties with regard to the aforementioned uses.

Pharmaceutically acceptable salts of peptides of this invention comprise the salts produced by the addition of acid, which are formed from inorganic acids and carboxylic acids. The compounds that are represented by Formulas (I), (II), (III), (IV), and (V) are prepared by known methods of peptide coupling.

In a preferred embodiment, the compounds pursuant to the invention exist as a mixture of compounds that is characterized by containing at least two of the compounds pursuant to the invention. It is particularly preferable to select the at least two compounds pursuant to the invention from one of the compounds (I), (II), (III), (IV), or (V). Preferred pharmaceutically acceptable salts of the compounds are formed with an inorganic acid. It is especially preferred in this case to form a pharmaceutically acceptable salt with hydrochloric acid, chloric acid, hydrobromic acid, bromic acid, and/or another halogen acid. Another preferred embodiment consists of the formation of a pharmaceutically acceptable salt with sulfuric acid and/or phosphoric acid. A pharmaceutically acceptable salt can also be formed advantageously with an organic acid. Especially preferred in this case is the formation of the pharmaceutically acceptable salt with acetic acid, propionic acid, malonic acid, maleic acid, citric acid, succinic acid, fumaric acid, malic acid, benzoic acid, and/or a similar carboxylic acid. The salts formed by the addition of acid are prepared by conventional methods, for example by neutralizing the free bases of the compounds (I), (II), (III), (IV), or (V) with the acid.

The substances pursuant to the invention can be used in compounds and for the inhibition of all thrombin-mediated or thrombin-associated functions. Pharmaceutical compositions that contain these molecules, as well as methods for the treatment and prophylaxis of vascular disorders, inflammatory reaction, carcinomas, and neurodegenerative diseases that use these compounds, are likewise part of this invention. The substances can also be used in compositions for ex vivo preparation, for the storage and treatment of blood outside the body, and for coating invasive equipment. The compounds pursuant to the invention can also be administered to a patient (patient in this context means a human or an animal) in combination with a fibrinolytic agent to increase the efficacy of a given dose or to reduce the dose necessary to produce a desired effect, such as the disintegration of a blood clot or to prevent the reocclusion of the previously blocked blood vessel.

Because of their high potential and the fact that they can be prepared by chemical synthesis techniques, the substances pursuant to the invention can be produced economically in commercially practical amounts. It is preferred to convert the peptides into suitable salt forms such as acetates or sulfates.

The invention also relates to drugs that are characterized by their content of one or more compounds pursuant to the invention, selected especially from one of the compounds (I), (II), (III), (IV), or (V), with the usual carriers, auxiliaries, or additives as the case may be. A diagnostic composition containing one or more of these compounds selected especially from the one of the compounds (I), (II), (III), (IV), or (V) is also an object of the invention.

Another object of the invention consists of the use of the compound as a thrombin inhibitor and for the preparation of a drug for thrombin inhibition, to inhibit fibrin formation, and/or to inhibit the formation of an agglutinative thrombus.

The use of one or more of the compounds, in particular those selected from one of the compounds (I), (II), (III), (IV), or (V), to prepare a diagnostic composition is likewise an object of the invention.

In one of the especially preferred embodiments for the preparation of the diagnostic composition, a compound pursuant to the invention is used in which $Y^2$ in the formulas (I), (II), (III), (IV), or (V) is 7-amido-3-methycoumarin or para-nitroanilide.

The compounds pursuant to the invention have a multitude of advantages over thrombin inhibitors known up to now. In particular, the peptides can be readily synthesized, are already effective with little modification, and have high efficacy accompanied by high specificity and low toxicity. Furthermore, the small peptides, as opposed to hirudin and hirulog, serve as lead structures for drugs that are preferably available orally.

The following Examples are intended to explain the invention in further detail, without limiting it.

EXAMPLE 1

N-Acetyl-L-Arg-L-Cha-L-Nle-L-Cha-D-Gln amide

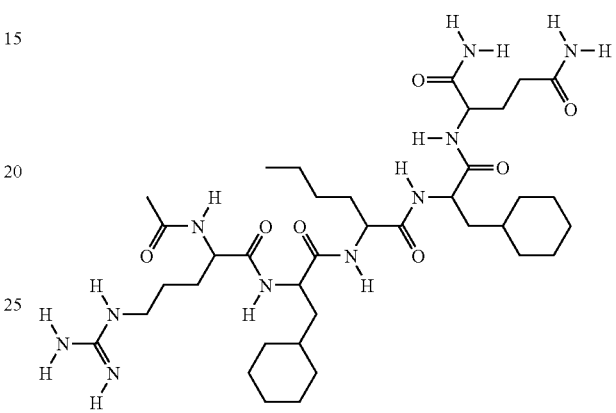

This peptide was prepared by solid phase synthesis with the aid of an ABIMED Synthesizer AMS 96 (ABIMED Analysen-Technik GmbH, Langenfeld, Germany). In detail, 1 mEq of Rink amide resin was reacted sequentially with 2×5 mEq of protected amino acid. The activation was carried out with 2×5 mEq of TBTU (O-benzotriazol-1-yl)-N,N,N',N'-tetramethyluronium tetrafluoroborate. After up to 6 cycles of synthesis, the N-terminus was acetylated with acetic anhydride. Then the peptide was deprotected by treatment with 90% TFA, 2.5% triisopropylsilane, 2.5% $H_2O$, and 5% dichloromethane. The peptide was decoupled from its carrier in the same step. The test compound was partly dissolved in 20 μL of trifluoroacetic acid after a drying step, and then incubated with 2×750 μL of cold butyl ether at −20° Celsius. After centrifugation, the supernatant was removed and the residual ether was evaporated. The identity of the products was confirmed by means of random sampling by mass spectroscopy.

Thrombin inhibition was determined by in vitro inhibition of thrombin amidase activity and constitutes 66% at a peptide concentration of 25 μM. The values of the inhibition constant $K_i$ were obtained from assays, in which thrombin hydrolyzes the fluorogenic substrate Tos-Gly-Pro-Arg-(7-amino-4-methylcoumarin). The assays were performed in 30 μL of assay buffer (0.05 M Tris, 0.1 M NaCl, 0.1% PEG 8000, pH 7.6) with 10 μL of human thrombin solution ($10^{-5}$ U/μL in assay buffer) and 140 μL of a solution of the fluorogenic substrate in assay buffer at a concentration v of 30 μM. Solutions of the test compound (10 μL) were added at various concentrations. The rates of substrate hydrolysis were measured by monitoring the reactions of 7-amino-4-methylcoumarin release at 460 nm with use of AMC. The reaction reached a steady state within 3 minutes after thrombin was combined with the substrate and an inhibitor. The kinetic data of the competitive inhibition ($K_m$, $V_{max}$, and $K_i$) were analyzed with the aid of the Hanes plot (A/V vs. A at various i values).

EXAMPLE 2

N-Acetyl-L-Arg-L-Cha-L-Asp-L-Cha amide

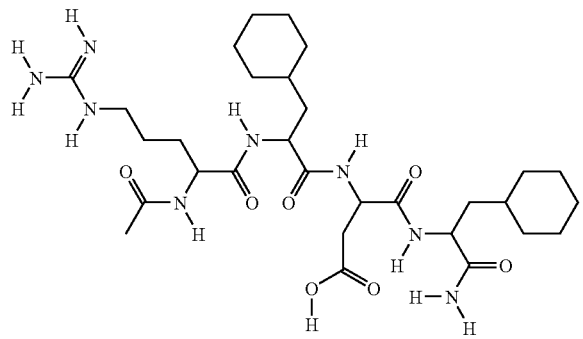

This peptide was synthesized as described in Example 1 and prepared for use in the assay.

Thrombin inhibition was determined by in vitro inhibition of thrombin amidase activity as in Exemplary Embodiment 1 and constitutes 68% at a peptide concentration of 25 μM.

EXAMPLE 3

N-Acetyl-L-Arg-L-Cha-L-Nle-L-Cha-L-Orn amide

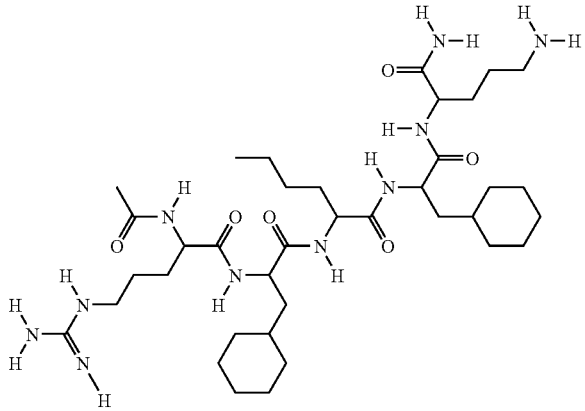

This peptide was synthesized as described in Example 1 and prepared for use in the assay.

Thrombin inhibition was determined by in vitro inhibition of thrombin amidase activity as in Exemplary Embodiment 1 and constitutes 63% at a peptide concentration of 10 μM.

EXAMPLE 4

N-Acetyl-L-Arg-L-Cha-L-Cha-L-Cha-D-Glu amide

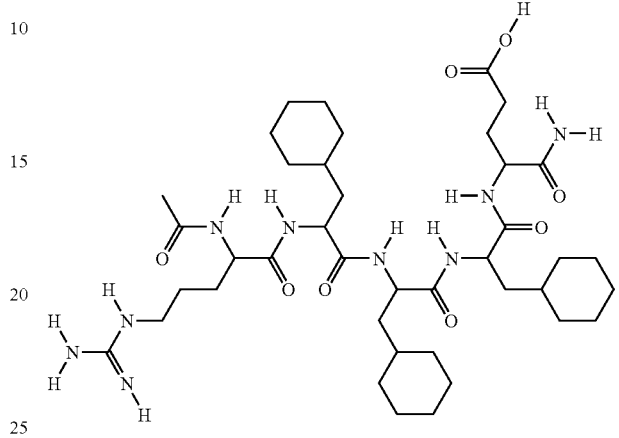

This peptide was synthesized as described in Example 1 and prepared for use in the assay.

Thrombin inhibition was determined by in vitro inhibition of thrombin amidase activity as in Exemplary Embodiment 1 and constitutes 78% at a peptide concentration of 10 μM.

EXAMPLE 5

N-Acetyl-L-Arg-L-Cha-D-Pro-D-Tyr-L-Arg amide

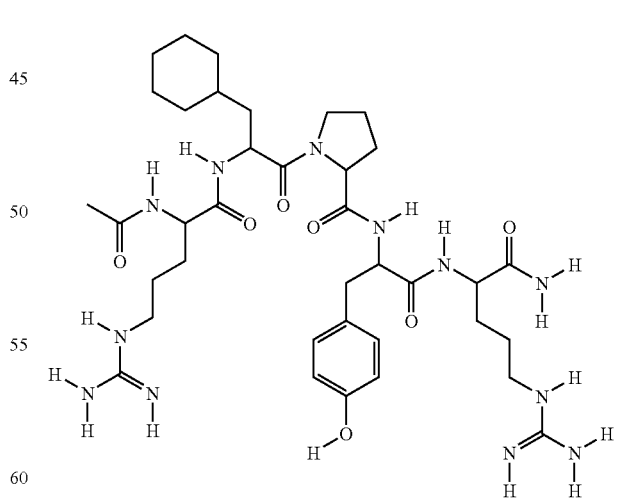

This peptide was synthesized as described in Example 1 and prepared for use in the assay.

Thrombin inhibition was determined by in vitro inhibition of thrombin amidase activity as in Exemplary Embodiment 1 and constitutes 98% at a peptide concentration of 10 μM.

EXAMPLE 6

N-Acetyl-L-Arg-L-Cha-L-Cha-L-Cha-L-Orn amide

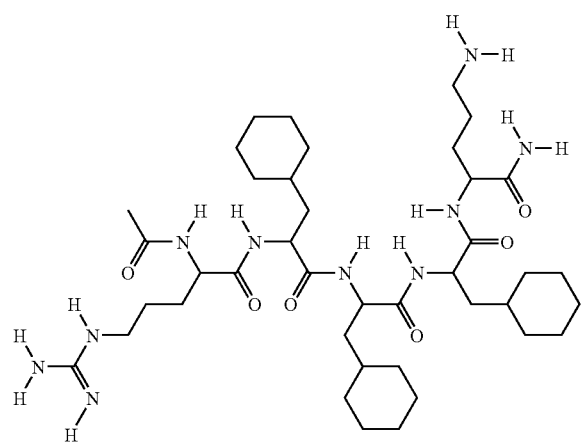

This peptide was synthesized as described in Example 1 and prepared for use in the assay.

Thrombin inhibition was determined by in vitro inhibition of thrombin amidase activity as in Exemplary Embodiment 1 and constitutes 71% at a peptide concentration of 10 μM.

EXAMPLE 7

N-Acetyl-L-Arg-L-Cha-L-Nle-L-Cha amide

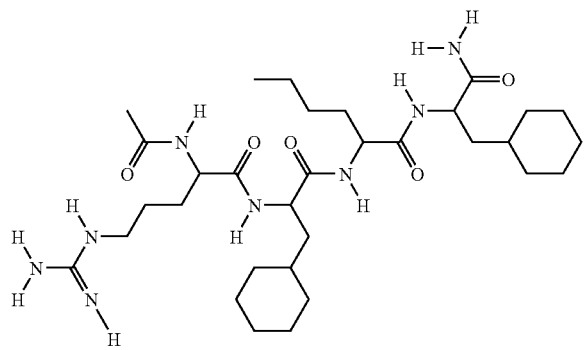

This peptide was synthesized as described in Example 1 and prepared for use in the assay.

Thrombin inhibition was determined by in vitro inhibition of thrombin amidase activity as in Exemplary Embodiment 1 and constitutes 60% at a peptide concentration of 10 μM.

EXAMPLE 8

N-Acetyl-L-Arg-L-Cha-L-Nle-L-Cha-D-Glu amide

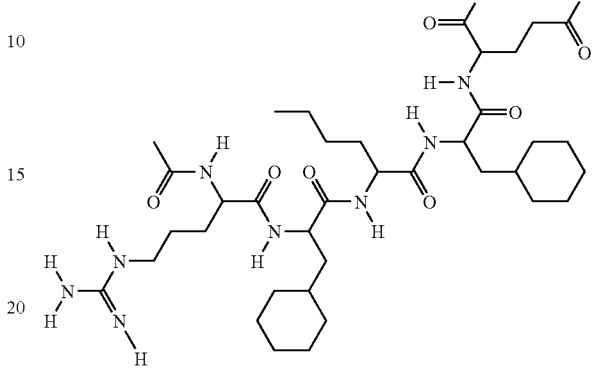

This peptide was synthesized as described in Example 1 and prepared for use in the assay.

Thrombin inhibition was determined by in vitro inhibition of thrombin amidase activity as in Exemplary Embodiment 1 and constitutes 35% at a peptide concentration of 1 μM.

EXAMPLE 9

N-Acetyl-D-Val-L-Ala-L-Cha-D-Pro-D-Tyr-L-Arg amide

This peptide was prepared by solid phase synthesis with use of an ABIMED Synthesizer AMS 96 (ABIMED Analysen-Technik GmbH, Langenfeld, Germany). In detail, 1 mEq of Rink amide resin was reacted sequentially with 2×5 mEq of protected amino acid. The activation was carried out with 2×5 mEq of TBTU (O-benzotriazol-1-yl)-N,N,N',N'-tetramethyluronium tetrafluoroborate. After up to 6 cycles of synthesis, the N-terminus was acetylated with acetic anhydride. Then the peptide was deprotected by treatment with 90% TFA, 2.5% triisopropylsilane, 2.5% $H_2O$, and 5% dichloromethane. The peptide was decoupled from its carrier in the same step. The test compound was partly dissolved in 20 μL of trifluoroacetic acid after a drying step, and then incubated with 2×750 μL of cold butyl ether at −20° Celsius. After centrifugation, the supernatant was removed and the residual ether was evaporated. The identity of the products was confirmed by means of random sampling by mass spectroscopy.

Thrombin inhibition was determined by in vitro inhibition of thrombin amidase activity and constitutes 53% at a peptide concentration of 1 μM. The values of the inhibition constant $K_i$ were obtained from assays, in which thrombin hydrolyzes the fluorogenic substrate Tos-Gly-Pro-Arg-(7-amino-4-methylcoumarin). The assays were performed in 30 μL of assay buffer (0.05 M Tris, 0.1 M NaCl, 0.1% PEG 8000, pH 7.6) with 10 μL of human thrombin solution ($10^{-5}$ U/μL in assay buffer) and 140 μL of a solution of the fluorogenic substrate in assay buffer at a concentration of 30 μM. Solutions of the test compound (10 μL) were added at various concentrations. The rates of substrate hydrolysis were measured by monitoring the reactions of 7-amino-4-methylcoumarin release at 460 nm with use of AMC. The reaction reached a steady state within 3 minutes after thrombin was combined with the substrate and an inhibitor. The kinetic data of the competitive inhibition ($K_m$, $V_{max}$, and $K_i$) were analyzed using the Hanes plot (A/V vs. A at various values for A; here, A is the substrate concentration and V the reaction rate).

EXAMPLE 10

N-Acetyl-L-Asp-L-Ser-L-Cha-D-Pro-D-Tyr-L-Arg amide

This peptide was synthesized as described in Example 9 and prepared for use in the assay.
Thrombin inhibition was determined by in vitro inhibition of thrombin amidase activity as in Exemplary Embodiment 9 and constitutes 51% at a peptide concentration of 1 μM.

EXAMPLE 11

N-Acetyl-L-Ile-L-Cha-D-Pro-D-Tyr-L-Arg amide

This peptide was synthesized as described in Example 9 and prepared for use in the assay.
Thrombin inhibition was determined by in vitro inhibition of thrombin amidase activity as in Exemplary Embodiment 9 and constitutes 48% at a peptide concentration of 1 μM.

EXAMPLE 12

N-Acetyl-D-Val-L-Cha-D-Pro-D-Tyr-L-Arg amide

This peptide was synthesized as described in Example 9 and prepared for use in the assay.
Thrombin inhibition was determined by in vitro inhibition of thrombin amidase activity as in Exemplary Embodiment 9 and constitutes 46% at a peptide concentration of 1 μM.

EXAMPLE 13

N-Acetyl-L-Ser-L-Ser-L-Cha-D-Pro-D-Tyr-L-Arg amide

This peptide was synthesized as described in Example 9 and prepared for use in the assay.
Thrombin inhibition was determined by in vitro inhibition of thrombin amidase activity as in Exemplary Embodiment 9 and constitutes 49% at a peptide concentration of 1 μM.

EXAMPLE 14

N-Acetyl-D-Lys-D-Pro-L-Cha-D-Pro-D-Tyr-L-Arg amide

This peptide was synthesized as described in Example 9 and prepared for use in the assay.
Thrombin inhibition was determined by in vitro inhibition of thrombin amidase activity as in Exemplary Embodiment 9 and constitutes 53% at a peptide concentration of 1 μM.

EXAMPLE 15

N-Acetyl-L-Tyr-L-Cit-L-Cha-D-Pro-D-Tyr-L-Arg amide

This peptide was synthesized as described in Example 9 and prepared for use in the assay.
Thrombin inhibition was determined by in vitro inhibition of thrombin amidase activity as in Exemplary Embodiment 9 and constitutes 51% at a peptide concentration of 1 μM.

EXAMPLE 16

N-Acetyl-L-Ser-D-Val-L-Cha-D-Pro-D-Tyr-L-Arg amide

This peptide was synthesized as described in Example 9 and prepared for use in the assay.
Thrombin inhibition was determined by in vitro inhibition of thrombin amidase activity as in Exemplary Embodiment 9 and constitutes 48% at a peptide concentration of 1 μM.

EXAMPLE 17

N-Acetyl-L-Ser-L-Ala-L-Cha-D-Pro-D-Tyr-L-Arg amide

This peptide was synthesized as described in Example 9 and prepared for use in the assay.
Thrombin inhibition was determined by in vitro inhibition of thrombin amidase activity as in Exemplary Embodiment 9 and constitutes 48% at a peptide concentration of 1 μM.

EXAMPLE 18

N-Acetyl-L-Ser-L-Arg-L-Cha-D-Pro-D-Tyr-L-Arg amide

This peptide was synthesized as described in Example 9 and prepared for use in the assay.
Thrombin inhibition was determined by in vitro inhibition of thrombin amidase activity as in Exemplary Embodiment 9 and constitutes 67% at a peptide concentration of 1 μM.

EXAMPLE 19

N-Acetyl-L-Ser-L-Cha-L-Cha-D-Pro-D-Tyr-L-Arg amide

This peptide was synthesized as described in Example 9 and prepared for use in the assay.
Thrombin inhibition was determined by in vitro inhibition of thrombin amidase activity as in Exemplary Embodiment 9 and constitutes 43% at a peptide concentration of 1 μM.

EXAMPLE 20

N-Acetyl-D-Lys-L-Nle-L-Cha-D-Pro-D-Tyr-L-Arg amide

This peptide was synthesized as described in Example 9 and prepared for use in the assay.
Thrombin inhibition was determined by in vitro inhibition of thrombin amidase activity as in Exemplary Embodiment 9 and constitutes 44% at a peptide concentration of 1 μM.

EXAMPLE 21

N-Acetyl-L-Arg-L-Cha-D-Pro-D-Tyr-L-Arg amide

This peptide was synthesized as described in Example 9 and prepared for use in the assay.

Thrombin inhibition was determined by in vitro inhibition of thrombin amidase activity as in Exemplary Embodiment 9 and constitutes 38% at a peptide concentration of 1 µM.

EXAMPLE 22

N-Acetyl-L-Ser-L-Cha-D-Pro-D-Tyr-L-Arg amide

This peptide was synthesized as described in Example 9 and prepared for use in the assay.
Thrombin inhibition was determined by in vitro inhibition of thrombin amidase activity as in Exemplary Embodiment 9 and constitutes 31% at a peptide concentration of 1 µM.

EXAMPLE 23

N-Acetyl-L-Ser-D-Glu-L-Cha-D-Pro-D-Tyr-L-Arg amide

This peptide was synthesized as described in Example 9 and prepared for use in the assay.
Thrombin inhibition was determined by in vitro inhibition of thrombin amidase activity as in Exemplary Embodiment 9 and constitutes 21% at a peptide concentration of 1 µM.

EXAMPLE 24

N-Acetyl-D-Tyr-L-Cha-D-Pro-D-Tyr-L-Arg amide

This peptide was synthesized as described in Example 9 and prepared for use in the assay.
Thrombin inhibition was determined by in vitro inhibition of thrombin amidase activity as in Exemplary Embodiment 9 and constitutes 27% at a peptide concentration of 1 µM.

EXAMPLE 25

N-Acetyl-D-Gln-D-His-L-Cha-D-Pro-D-Tyr-L-Arg amide

This peptide was prepared by solid phase synthesis with use of an ABIMED Synthesizer AMS 96 (ABIMED Analysen-Technik GmbH, Langenfeld, Germany). In detail, 1 mEq of Rink amide resin was reacted sequentially with 2×5 mEq of protected amino acid. The activation was carried out with 2×5 mEq of TBTU (O-benzotriazol-1-yl)-N,N,N',N'-tetramethyluronium tetrafluoroborate. After up to 6 cycles of synthesis, the N-terminus was acetylated with acetic anhydride. Then the peptide was deprotected by treatment with 90% TFA, 2.5% triisopropylsilane, 2.5% $H_2O$, and 5% dichloromethane. The peptide was decoupled from its carrier in the same step. The test compound was partly dissolved in 20 µL of trifluoroacetic acid after a drying step, and then incubated with 2×750 µL of cold butyl ether at −20° Celsius. After centrifugation, the supernatant was removed and the residual ether was evaporated. The identity of the products was confirmed by means of random sampling by mass spectroscopy.

Thrombin inhibition was determined by in vitro inhibition of thrombin amidase activity and constitutes 59% at a peptide concentration of 1 µM. The values of the inhibition constant $K_i$ were obtained from assays, in which thrombin hydrolyzes the fluorogenic substrate Tos-Gly-Pro-Arg-(7-amino-4-methylcoumarin). The assays were performed in 30 µL of assay buffer (0.05 M Tris, 0.1 M NaCl, 0.1% PEG 8000, pH 7.6) with 10 µL of human thrombin solution ($10^{-5}$ U/µL in assay buffer) and 140 µL of a solution of the fluorogenic substrate in assay buffer at a concentration of 30 µM. Solutions of the test compound (10 µL) were added at various concentrations. The rates of substrate hydrolysis were measured by monitoring the reactions of 7-amino-4-methylcoumarin release at 460 nm with use of AMC. The reaction reached a steady state within 3 minutes after thrombin was combined with the substrate and an inhibitor. The kinetic data of the competitive inhibition ($K_m$, $V_{max}$, and $K_i$) were analyzed using the Hanes plot (A/V vs. A at various values for A; here, A is the substrate concentration and V the reaction rate).

EXAMPLE 26

N-Acetyl-D-Glu-L-Cha-D-Pro-D-Tyr-L-Arg amide

This peptide was synthesized as described in Example 25 and prepared for use in the assay.
Thrombin inhibition was determined by in vitro inhibition of thrombin amidase activity as in Exemplary Embodiment 25 and constitutes 58% at a peptide concentration of 1 µM.

EXAMPLE 27

N-Acetyl-D-Val-D-His-L-Cha-D-Pro-D-Tyr-L-Arg amide

This peptide was synthesized as described in Example 25 and prepared for use in the assay.
Thrombin inhibition was determined by in vitro inhibition of thrombin amidase activity as in Exemplary Embodiment 25 and constitutes 51% at a peptide concentration of 1 µM.

EXAMPLE 28

N-Acetyl-L-Ala-L-Cha-D-Pro-D-Tyr-L-Arg amide

This peptide was synthesized as described in Example 25 and prepared for use in the assay.
Thrombin inhibition was determined by in vitro inhibition of thrombin amidase activity as in Exemplary Embodiment 25 and constitutes 44% at a peptide concentration of 1 µM.

EXAMPLE 29

N-Acetyl-L-Ile-L-Arg-L-Cha-D-Pro-D-Tyr-L-Arg amide

This peptide was synthesized as described in Example 25 and prepared for use in the assay.
Thrombin inhibition was determined by in vitro inhibition of thrombin amidase activity as in Exemplary Embodiment 25 and constitutes 61% at a peptide concentration of 1 µM.

EXAMPLE 30

N-Acetyl-L-Tyr-L-Cit-L-Cha-D-Pro-D-Tyr-L-Arg amide

This peptide was synthesized as described in Example 25 and prepared for use in the assay.
Thrombin inhibition was determined by in vitro inhibition of thrombin amidase activity as in Exemplary Embodiment 25 and constitutes 55% at a peptide concentration of 1 µM.

EXAMPLE 31

N-Acetyl-L-Ser-L-Ser-L-Cha-D-Pro-D-Tyr-L-Arg amide

This peptide was synthesized as described in Example 25 and prepared for use in the assay.

Thrombin inhibition was determined by in vitro inhibition of thrombin amidase activity as in Exemplary Embodiment 25 and constitutes 40% at a peptide concentration of 1 µM.

EXAMPLE 32

N-Acetyl-D-Val-L-Cha-D-Pro-D-Tyr-L-Arg amide

This peptide was synthesized as described in Example 25 and prepared for use in the assay.

Thrombin inhibition was determined by in vitro inhibition of thrombin amidase activity as in Exemplary Embodiment 25 and constitutes 45% at a peptide concentration of 1 µM.

EXAMPLE 33

N-Acetyl-L-Trp-L-Cha-D-Pro-D-Tyr-L-Arg amide

This peptide was synthesized as described in Example 25 and prepared for use in the assay.

Thrombin inhibition was determined by in vitro inhibition of thrombin amidase activity as in Exemplary Embodiment 25 and constitutes 63% at a peptide concentration of 1 µM.

EXAMPLE 34

N-Acetyl-L-Ser-L-Ala-L-Cha-D-Pro-D-Tyr-L-Arg amide

This peptide was synthesized as described in Example 25 and prepared for use in the assay.

Thrombin inhibition was determined by in vitro inhibition of thrombin amidase activity as in Exemplary Embodiment 25 and constitutes 47% at a peptide concentration of 1 µM.

EXAMPLE 35

N-Acetyl-L-Ser-L-Arg-L-Cha-D-Pro-D-Tyr-L-Arg amide

This peptide was synthesized as described in Example 25 and prepared for use in the assay.

Thrombin inhibition was determined by in vitro inhibition of thrombin amidase activity as in Exemplary Embodiment 25 and constitutes 51% at a peptide concentration of 1 µM.

EXAMPLE 36

N-Acetyl-D-Lys-L-Nle-L-Cha-D-Pro-D-Tyr-L-Arg amide

This peptide was synthesized as described in Example 25 and prepared for use in the assay.

Thrombin inhibition was determined by in vitro inhibition of thrombin amidase activity as in Exemplary Embodiment 25 and constitutes 48% at a peptide concentration of 1 µM.

EXAMPLE 37

N-Acetyl-D-Tyr-L-Cha-D-Pro-D-Tyr-L-Arg amide

This peptide was synthesized as described in Example 25 and prepared for use in the assay.

Thrombin inhibition was determined by in vitro inhibition of thrombin amidase activity as in Exemplary Embodiment 25 and constitutes 47% at a peptide concentration of 1 µM.

EXAMPLE 38

N-Acetyl-L-Arg-L-Cha-D-Pro-D-Tyr-L-Arg amide

This peptide was synthesized as described in Example 25 and prepared for use in the assay.

Thrombin inhibition was determined by in vitro inhibition of thrombin amidase activity as in Exemplary Embodiment 25 and constitutes 47% at a peptide concentration of 1 µM.

EXAMPLE 39

N-Acetyl-L-Tyr-D-Pro-L-Cha-D-Pro-D-Tyr-L-Arg amide

This peptide was synthesized as described in Example 25 and prepared for use in the assay.

Thrombin inhibition was determined by in vitro inhibition of thrombin amidase activity as in Exemplary Embodiment 25 and constitutes 44% at a peptide concentration of 1 µM.

EXAMPLE 40

N-Acetyl-D-Gln-D-His-L-Cha-D-Pro-D-Tyr-L-Arg amide

This peptide was prepared by solid phase synthesis with use of an ABIMED Synthesizer AMS 96 (ABIMED Analysen-Technik GmbH, Langenfeld, Germany). In detail, 1 mEq of Rink amide resin was reacted sequentially with 2×5 mEq of protected amino acid. The activation was carried out with 2×5 mEq of TBTU (O-benzotriazol-1-yl)-N,N,N',N'-tetramethyluronium tetrafluoroborate. After up to 6 cycles of synthesis, the N-terminus was acetylated with acetic anhydride. Then the peptide was deprotected by treatment with 90% TFA, 2.5% triisopropylsilane, 2.5% H$_2$O, and 5% dichloromethane. The peptide was decoupled from its carrier in the same step. The test compound was partly dissolved in 20 µL of trifluoroacetic acid after a drying step, and then incubated with 2×750 µL of cold butyl ether at −20° Celsius. After centrifugation, the supernatant was removed and the residual ether was evaporated. The identity of the products was confirmed by means of random sampling by mass spectroscopy.

Thrombin inhibition was determined by in vitro inhibition of thrombin amidase activity and constitutes 59% at a peptide concentration of 1 µM. The values of the inhibition constant K$_i$ were obtained from assays, in which thrombin hydrolyzes the fluorogenic substrate Tos-Gly-Pro-Arg-(7-amino-4-methylcoumarin). The assays were conducted in 30 µL of assay buffer (0.05 M Tris, 0.1 M NaCl, 0.1% PEG 8000, pH 7.6) with 10 µL of human thrombin solution ($10^{-5}$ U/µL in assay buffer) and 140 µL of a solution of the fluorogenic substrate in assay buffer at a concentration of 30 µM. Solutions of the test compound (10 µL) were added at various concentrations. The rates of substrate hydrolysis were measured by monitoring the reactions of 7-amino-4- methylcoumarin release at 460 nm with use of AMC. The reaction reached a steady state within 3 minutes after thrombin was combined with the substrate and an inhibitor. The kinetic data of the competitive inhibition ($K_m$, $V_{max}$, and $K_i$) were analyzed using the Hanes plot (A/V vs. A at various values for A; here, A is the substrate concentration and V the reaction rate).

EXAMPLE 41

N-Acetyl-D-Glu-L-Cha-D-Pro-D-Tyr-L-Arg amide

This peptide was synthesized as described in Example 40 and prepared for use in the assay.

Thrombin inhibition was determined by in vitro inhibition of thrombin amidase activity as in Exemplary Embodiment 40 and constitutes 58% at a peptide concentration of 1 μM.

EXAMPLE 42

N-Acetyl-D-Val-D-His-L-Cha-D-Pro-D-Tyr-L-Arg amide

This peptide was synthesized as described in Example 40 and prepared for use in the assay.

Thrombin inhibition was determined by in vitro inhibition of thrombin amidase activity as in Exemplary Embodiment 40 and constitutes 51% at a peptide concentration of 1 μM.

EXAMPLE 43

N-Acetyl-L-Ala-L-Cha-D-Pro-D-Tyr-L-Arg amide

This peptide was synthesized as described in Example 40 and prepared for use in the assay.

Thrombin inhibition was determined by in vitro inhibition of thrombin amidase activity as in Exemplary Embodiment 40 and constitutes 44% at a peptide concentration of 1 μM.

EXAMPLE 44

N-Acetyl-L-Ile-L-Arg-L-Cha-D-Pro-D-Tyr-L-Arg amide

This peptide was synthesized as described in Example 40 and prepared for use in the assay.

Thrombin inhibition was determined by in vitro inhibition of thrombin amidase activity as in Exemplary Embodiment 40 and constitutes 61% at a peptide concentration of 1 μM.

EXAMPLE 45

N-Acetyl-L-Tyr-L-Cit-L-Cha-D-Pro-D-Tyr-L-Arg amide

This peptide was synthesized as described in Example 40 and prepared for use in the assay.

Thrombin inhibition was determined by in vitro inhibition of thrombin amidase activity as in Exemplary Embodiment 40 and constitutes 55% at a peptide concentration of 1 μM.

EXAMPLE 46

N-Acetyl-L-Ser-L-Ser-L-Cha-D-Pro-D-Tyr-L-Arg amide

This peptide was synthesized as described in Example 40 and prepared for use in the assay.

Thrombin inhibition was determined by in vitro inhibition of thrombin amidase activity as in Exemplary Embodiment 40 and constitutes 40% at a peptide concentration of 1 μM.

EXAMPLE 47

N-Acetyl-D-Val-L-Cha-D-Pro-D-Tyr-L-Arg amide

This peptide was synthesized as described in Example 40 and prepared for use in the assay.

Thrombin inhibition was determined by in vitro inhibition of thrombin amidase activity as in Exemplary Embodiment 40 and constitutes 45% at a peptide concentration of 1 μM.

EXAMPLE 48

N-Acetyl-L-Trp-L-Cha-D-Pro-D-Tyr-L-Arg amide

This peptide was synthesized as described in Example 40 and prepared for use in the assay.

Thrombin inhibition was determined by in vitro inhibition of thrombin amidase activity as in Exemplary Embodiment 40 and constitutes 63% at a peptide concentration of 1 μM.

EXAMPLE 49

N-Acetyl-L-Ser-L-Ala-L-Cha-D-Pro-D-Tyr-L-Arg amide

This peptide was synthesized as described in Example 40 and prepared for use in the assay.

Thrombin inhibition was determined by in vitro inhibition of thrombin amidase activity as in Exemplary Embodiment 40 and constitutes 47% at a peptide concentration of 1 μM.

EXAMPLE 50

N-Acetyl-L-Ser-L-Arg-L-Cha-D-Pro-D-Tyr-L-Arg amide

This peptide was synthesized as described in Example 40 and prepared for use in the assay.

Thrombin inhibition was determined by in vitro inhibition of thrombin amidase activity as in Exemplary Embodiment 40 and constitutes 51% at a peptide concentration of 1 μM.

EXAMPLE 51

N-Acetyl-D-Lys-L-Nle-L-Cha-D-Pro-D-Tyr-L-Arg amide

This peptide was synthesized as described in Example 40 and prepared for use in the assay.

Thrombin inhibition was determined by in vitro inhibition of thrombin amidase activity as in Exemplary Embodiment 40 and constitutes 48% at a peptide concentration of 1 μM.

EXAMPLE 52

N-Acetyl-D-Tyr-L-Cha-D-Pro-D-Tyr-L-Arg amide

This peptide was synthesized as described in Example 40 and prepared for use in the assay.

Thrombin inhibition was determined by in vitro inhibition of thrombin amidase activity as in Exemplary Embodiment 40 and constitutes 47% at a peptide concentration of 1 µM.

EXAMPLE 53

N-Acetyl-L-Arg-L-Cha-D-Pro-D-Tyr-L-Arg amide

This peptide was synthesized as described in Example 40 and prepared for use in the assay.

Thrombin inhibition was determined by in vitro inhibition of thrombin amidase activity as in Exemplary Embodiment 40 and constitutes 47% at a peptide concentration of 1 µM.

EXAMPLE 54

N-Acetyl-L-Tyr-D-Pro-L-Cha-D-Pro-D-Tyr-L-Arg amide

This peptide was synthesized as described in Example 40 and prepared for use in the assay.

Thrombin inhibition was determined by in vitro inhibition of thrombin amidase activity as in Exemplary Embodiment 40 and constitutes 44% at a peptide concentration of 1 µM.

EXAMPLE 55

N-Acetyl-L-Ala-D-Cha-L-Aze-D-Tyr-L-Arg amide

This peptide was synthesized as described in Example 40 and prepared for use in the assay.

Thrombin inhibition was determined by in vitro inhibition of thrombin amidase activity as in Exemplary Embodiment 40 and constitutes 63% at a peptide concentration of 1 µM.

EXAMPLE 56

N-Acetyl-L-Ala-D-Cha-L-Pro-D-Tyr-L-Har amide

This peptide was synthesized as described in Example 40 and prepared for use in the assay.

Thrombin inhibition was determined by in vitro inhibition of thrombin amidase activity as in Exemplary Embodiment 40 and constitutes 56% at a peptide concentration of 1 µM.

EXAMPLE 57

N-Acetyl-L-Ala-D-Cha-L-Aze-D-Tyr-L-Har amide

This peptide was synthesized as described in Example 40 and prepared for use in the assay.

Thrombin inhibition was determined by in vitro inhibition of thrombin amidase activity as in Exemplary Embodiment 40 and constitutes 83% at a peptide concentration of 1 µM.

EXAMPLE 58

N-Acetyl-D-Gln-D-His-L-Cha-D-Pro-D-Tyr-L-Arg amide

This peptide was prepared by solid phase synthesis with use of an ABIMED Synthesizer AMS 96 (ABIMED Analysen-Technik GmbH, Langenfeld, Germany). In detail, 1 mEq of Rink amide resin was reacted sequentially with 2×5 mEq of protected amino acid. The activation was carried out with 2×5 mEq of TBTU (O-benzotriazol-1-yl)-N,N,N',N'-tetramethyluronium tetrafluoroborate. After up to 6 cycles of synthesis, the N-terminus was acetylated with acetic anhydride. Then the peptide was deprotected by treatment with 90% TFA, 2.5% triisopropylsilane, 2.5% $H_2O$, and 5% dichloromethane. The peptide was decoupled from its carrier in the same step. The test compound was partly dissolved in 20 µL of trifluoroacetic acid after a drying step, and then incubated with 2×750 µL of cold butyl ether at −20° Celsius. After centrifugation, the supernatant was removed and the residual ether was evaporated. The identity of the products was confirmed by means of random sampling by mass spectroscopy.

Thrombin inhibition was determined by in vitro inhibition of thrombin amidase activity and constitutes 59% at a peptide concentration of 1 µM. The values of the inhibition constant $K_i$ were obtained from assays, in which thrombin hydrolyzes the fluorogenic substrate Tos-Gly-Pro-Arg-(7-amino-4-methylcoumarin). The assays were performed in 30 µL of assay buffer (0.05 M Tris, 0.1 M NaCl, 0.1% PEG 8000, pH 7.6) with 10 µL of human thrombin solution ($10^{-5}$ U/µL in assay buffer) and 140 µL of a solution of the fluorogenic substrate in assay buffer at a concentration of 30 µM. Solutions of the test compound (10 µL) were added at various concentrations. The rates of substrate hydrolysis were measured by monitoring the reactions of 7-amino-4-methylcoumarin release at 460 nm with use of AMC. The reaction reached a steady state within 3 minutes after thrombin was combined with the substrate and an inhibitor. The kinetic data of the competitive inhibition ($K_m$, $V_{max}$, and $K_i$) were analyzed using the Hanes plot (A/V vs. A at various values for A; here, A is the substrate concentration and V the reaction rate).

EXAMPLE 59

N-Acetyl-D-Glu-L-Cha-D-Pro-D-Tyr-L-Arg amide

This peptide was synthesized as described in Example 58 and prepared for use in the assay.

Thrombin inhibition was determined by in vitro inhibition of thrombin amidase activity as in Exemplary Embodiment 58 and constitutes 58% at a peptide concentration of 1 µM.

EXAMPLE 60

N-Acetyl-D-Val-D-His-L-Cha-D-Pro-D-Tyr-L-Arg amide

This peptide was synthesized as described in Example 58 and prepared for use in the assay.

Thrombin inhibition was determined by in vitro inhibition of thrombin amidase activity as in Exemplary Embodiment 58 and constitutes 51% at a peptide concentration of 1 µM.

EXAMPLE 61

N-Acetyl-L-Ala-L-Cha-D-Pro-D-Tyr-L-Arg amide

This peptide was synthesized as described in Example 58 and prepared for use in the assay.

Thrombin inhibition was determined by in vitro inhibition of thrombin amidase activity as in Exemplary Embodiment 58 and constitutes 44% at a peptide concentration of 1 μM.

EXAMPLE 62

N-Acetyl-L-Ile-L-Arg-L-Cha-D-Pro-D-Tyr-L-Arg amide

This peptide was synthesized as described in Example 58 and prepared for use in the assay.

Thrombin inhibition was determined by in vitro inhibition of thrombin amidase activity as in Exemplary Embodiment 58 and constitutes 61% at a peptide concentration of 1 μM.

EXAMPLE 63

N-Acetyl-L-Tyr-L-Cit-L-Cha-D-Pro-D-Tyr-L-Arg amide

This peptide was synthesized as described in Example 58 and prepared for use in the assay.

Thrombin inhibition was determined by in vitro inhibition of thrombin amidase activity as in Exemplary Embodiment 58 and constitutes 55% at a peptide concentration of 1 μM.

EXAMPLE 64

N-Acetyl-L-Ser-L-Ser-L-Cha-D-Pro-D-Tyr-L-Arg amide

This peptide was synthesized as described in Example 58 and prepared for use in the assay.

Thrombin inhibition was determined by in vitro inhibition of thrombin amidase activity as in Exemplary Embodiment 58 and constitutes 40% at a peptide concentration of 1 μM.

EXAMPLE 65

N-Acetyl-D-Val-L-Cha-D-Pro-D-Tyr-L-Arg amide

This peptide was synthesized as described in Example 58 and prepared for use in the assay.

Thrombin inhibition was determined by in vitro inhibition of thrombin amidase activity as in Exemplary Embodiment 58 and constitutes 45% at a peptide concentration of 1 μM.

EXAMPLE 66

N-Acetyl-L-Trp-L-Cha-D-Pro-D-Tyr-L-Arg amide

This peptide was synthesized as described in Example 58 and prepared for use in the assay.

Thrombin inhibition was determined by in vitro inhibition of thrombin amidase activity as in Exemplary Embodiment 58 and constitutes 63% at a peptide concentration of 1 μM.

EXAMPLE 67

N-Acetyl-L-Ser-L-Ala-L-Cha-D-Pro-D-Tyr-L-Arg amide

This peptide was synthesized as described in Example 58 and prepared for use in the assay.

Thrombin inhibition was determined by in vitro inhibition of thrombin amidase activity as in Exemplary Embodiment 58 and constitutes 47% at a peptide concentration of 1 μM.

EXAMPLE 68

N-Acetyl-L-Ser-L-Arg-L-Cha-D-Pro-D-Tyr-L-Arg amide

This peptide was synthesized as described in Example 58 and prepared for use in the assay.

Thrombin inhibition was determined by in vitro inhibition of thrombin amidase activity as in Exemplary Embodiment 58 and constitutes 51% at a peptide concentration of 1 μM.

EXAMPLE 69

N-Acetyl-D-Lys-L-Nle-L-Cha-D-Pro-D-Tyr-L-Arg amide

This peptide was synthesized as described in Example 58 and prepared for use in the assay.

Thrombin inhibition was determined by in vitro inhibition of thrombin amidase activity as in Exemplary Embodiment 58 and constitutes 48% at a peptide concentration of 1 μM.

EXAMPLE 70

N-Acetyl-D-Tyr-L-Cha-D-Pro-D-Tyr-L-Arg amide

This peptide was synthesized as described in Example 58 and prepared for use in the assay.

Thrombin inhibition was determined by in vitro inhibition of thrombin amidase activity as in Exemplary Embodiment 58 and constitutes 47% at a peptide concentration of 1 μM.

EXAMPLE 71

N-Acetyl-L-Arg-L-Cha-D-Pro-D-Tyr-L-Arg amide

This peptide was synthesized as described in Example 58 and prepared for use in the assay.

Thrombin inhibition was determined by in vitro inhibition of thrombin amidase activity as in Exemplary Embodiment 58 and constitutes 47% at a peptide concentration of 1 μM.

EXAMPLE 72

N-Acetyl-L-Tyr-D-Pro-L-Cha-D-Pro-D-Tyr-L-Arg amide

This peptide was synthesized as described in Example 58 and prepared for use in the assay.

Thrombin inhibition was determined by in vitro inhibition of thrombin amidase activity as in Exemplary Embodiment 58 and constitutes 44% at a peptide concentration of 1 μM.

EXAMPLE 73

N-Acetyl-L-Ala-D-Cha-L-Aze-D-Tyr-L-Arg amide

This peptide was synthesized as described in Example 58 and prepared for use in the assay.

Thrombin inhibition was determined by in vitro inhibition of thrombin amidase activity as in Exemplary Embodiment 58 and constitutes 63% at a peptide concentration of 1 µM.

EXAMPLE 74

N-Acetyl-L-Ala-D-Cha-L-Pro-D-Tyr-L-Har amide

This peptide was synthesized as described in Example 58 and prepared for use in the assay.

Thrombin inhibition was determined by in vitro inhibition of thrombin amidase activity as in Exemplary Embodiment 58 and constitutes 56% at a peptide concentration of 1 µM.

EXAMPLE 75

N-Acetyl-L-Trp-D-Cha-L-Aze-D-Tyr-L-Har amide

This peptide was synthesized as described in Example 58 and prepared for use in the assay.

Thrombin inhibition was determined by in vitro inhibition of thrombin amidase activity as in Exemplary Embodiment 58 and constitutes 76% at a peptide concentration of 250 nM.

EXAMPLE 76

N-Acetyl-L-Ala-D-Cha-L-Aze-D-Tyr-L-Har amide

This peptide was synthesized as described in Example 58 and prepared for use in the assay.

Thrombin inhibition was determined by in vitro inhibition of thrombin amidase activity as in Exemplary Embodiment 58 and constitutes 77% at a peptide concentration of 250 nM.

EXAMPLE 77

N-Acetyl-D-Phe-D-Cha-L-Aze-D-Tyr-L-Har amide

This peptide was synthesized as described in Example 58 and prepared for use in the assay.

Thrombin inhibition was determined by in vitro inhibition of thrombin amidase activity as in Exemplary Embodiment 58 and constitutes 77% at a peptide concentration of 250 nM.

EXAMPLE 78

N-Acetyl-L-Dcp-D-Cha-L-Aze-D-Tyr-L-Har amide

This peptide was synthesized as described in Example 58 and prepared for use in the assay.

Thrombin inhibition was determined by in vitro inhibition of thrombin amidase activity as in Exemplary Embodiment 58 and constitutes 75% at a peptide concentration of 250 nM.

EXAMPLE 79

N-Acetyl-L-Nhm-D-Cha-L-Aze-D-Tyr-L-Har amide

This peptide was synthesized as described in Example 58 and prepared for use in the assay.

Thrombin inhibition was determined by in vitro inhibition of thrombin amidase activity as in Exemplary Embodiment 58 and constitutes 80% at a peptide concentration of 250 nM.

EXAMPLE 80

N-Acetyl-L-Iq3-D-Cha-L-Aze-D-Tyr-L-Har amide

This peptide was synthesized as described in Example 58 and prepared for use in the assay.

Thrombin inhibition was determined by in vitro inhibition of thrombin amidase activity as in Exemplary Embodiment 58 and constitutes 72% at a peptide concentration of 250 nM.

EXAMPLE 81

N-Acetyl-L-Ppd-D-Cha-L-Aze-D-Tyr-L-Har amide

This peptide was synthesized as described in Example 58 and prepared for use in the assay.

Thrombin inhibition was determined by in vitro inhibition of thrombin amidase activity as in Exemplary Embodiment 58 and constitutes 76% at a peptide concentration of 250 nM.

EXAMPLE 82

N-Acetyl-L-Tea-D-Cha-L-Aze-D-Tyr-L-Har amide

This peptide was synthesized as described in Example 58 and prepared for use in the assay.

Thrombin inhibition was determined by in vitro inhibition of thrombin amidase activity as in Exemplary Embodiment 58 and constitutes 74% at a peptide concentration of 250 nM.

EXAMPLE 83

N-Acetyl-L-Phg-D-Cha-L-Aze-D-Tyr-L-Har amide

This peptide was synthesized as described in Example 58 and prepared for use in the assay.

Thrombin inhibition was determined by in vitro inhibition of thrombin amidase activity as in Exemplary Embodiment 58 and constitutes 95% at a peptide concentration of 250 nM.

EXAMPLE 84

N-Acetyl-L-Nle-D-Cha-L-Aze-D-Tyr-L-Har amide

This peptide was synthesized as described in Example 58 and prepared for use in the assay.

Thrombin inhibition was determined by in vitro inhibition of thrombin amidase activity as in Exemplary Embodiment

EXAMPLE 85

N-Acetyl-L-Cha-D-Cha-L-Aze-D-Tyr-L-Har amide

This peptide was synthesized as described in Example 58 and prepared for use in the assay.

Thrombin inhibition was determined by in vitro inhibition of thrombin amidase activity as in Exemplary Embodiment 58 and constitutes 90% at a peptide concentration of 250 nM.

EXAMPLE 86

N-Acetyl-L-Pnp-D-Cha-L-Aze-D-Tyr-L-Har amide

This peptide was synthesized as described in Example 58 and prepared for use in the assay.

Thrombin inhibition was determined by in vitro inhibition of thrombin amidase activity as in Exemplary Embodiment 58 and constitutes 72% at a peptide concentration of 250 nM.

Description of the Abbreviations
Ala=alanine
Val=valine
Leu=leucine
Ile=isoleucine
Pro=proline
Phe=phenylalanine
Phg=phenylglycine
Cha=cyclohexylalanine
Trp=tryptophan
Met=methionine
Gly=glycine
Ser=serine
Thr=threonine
Cys=cysteine
Tyr=tyrosine
Asn=asparagine
Gln=glutamine
Asp=aspartic acid
Glu=glutamic acid
Lys=lysine
Arg=arginine
His=histidine
Nle=norleucine
Orn=ornithine
Cit=citrulline
Aze=azetidine
Har=homoarginine
Dcp=dichlorophenylalanine
Nhm=tetrahydronorharman-3-carboxylic acid
Iq3=1,2,3,4-tetrahydroisoquinoline-3-carboxylic acid
Ppd=4-phenylpiperidine-4-carboxylic acid
Tea=thienylalanine
Pnp=para-nitrophenylalanine

---

---

The invention claimed is:

1. A compound or pharmaceutically acceptable salt thereof of the formula:

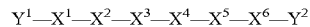

$Y^1-X^1-X^2-X^3-X^4-X^5-X^6-Y^2$ wherein, $Y^1$ is a hydrogen, a methyl, an acetyl or is characterized by a backbone consisting of 1 to 32 carbon atoms;

$X^1$ is absent or an L- or D- amino acid selected from the group consisting of Val, Ala, Leu, Ile, Nle, Asn, Gln, Ser, Thr, Tyr, Arg, Lys and Orn;

$X^2$ is absent or an L- or D- amino acid selected from the group consisting of Val, Ala, Leu, Ile, Nle, Ser, Thr, Tyr, Pro, Cit, Mg, Lys, Orn, His, Glu, Asp, Trp, Cha (cyclohexylalanine) and Chg (cyclohexylglycine);

$X^3$ is an L- or D- amino acid selected from the group consisting of Cha and Chg;

$X^4$ is an L- or D- amino acid selected from the group consisting of Pro and Aze (azetidine-2-carboxylic acid);

$X^5$ is an L- or D- amino acid selected from the group consisting of Tyr and Phe;

$X^6$ is absent or an L- or D- amino acid selected from the group consisting of Arg, Lys, Orn and Har (homoarginine); and $Y^2$ is a hydrogen, a hydroxyl, an amino, 7-amido-4-methylcoumarin or p-nitroanilide.

2. A pharmaceutical composition comprising an effective thrombus-preventing amount of a compound according to claim 1 and a pharmaceutically acceptable carrier.

3. The pharmaceutical composition of claim 2 further comprising carriers, auxiliaries, additives or combinations thereof.

4. A method for thrombin inhibition in humans and animals comprising administering an effective amount of a compound according to claim 1 to a human or animal in need thereof.

* * * * *